(12) United States Patent
Sussman et al.

(10) Patent No.: US 7,758,585 B2
(45) Date of Patent: Jul. 20, 2010

(54) PUMPING CHAMBER FOR A LIQUEFACTION HANDPIECE

(75) Inventors: Glenn Sussman, Laguna Nigel, CA (US); John R. Underwood, Laguna Nigel, CA (US)

(73) Assignee: Alcon, Inc., Hunenburg (CH)

( * ) Notice: Subject to any disclaimer, the term of this patent is extended or adjusted under 35 U.S.C. 154(b) by 886 days.

(21) Appl. No.: 11/082,085

(22) Filed: Mar. 16, 2005

(65) Prior Publication Data

US 2006/0212039 A1    Sep. 21, 2006

(51) Int. Cl.
*A61F 9/00* (2006.01)
(52) U.S. Cl. ...................................... 606/107
(58) Field of Classification Search .................. 604/27, 604/35; 606/107
See application file for complete search history.

(56) References Cited

U.S. PATENT DOCUMENTS

| | | |
|---|---|---|
| 121,697 A | 12/1871 | Wheatland |
| 294,334 A | 2/1884 | Reed et al. |
| 351,159 A | 10/1886 | Brengel |
| 865,631 A | 9/1907 | Cottler |
| 2,121,936 A | 6/1938 | Rosswell |
| 2,536,836 A | 1/1951 | Bowling |
| 2,623,725 A | 12/1952 | Sands |
| 3,085,589 A | 4/1963 | Sands |
| 3,191,807 A | 6/1965 | Rodrigues |
| 3,336,942 A | 8/1967 | Garland et al |
| 3,561,471 A | 2/1971 | Sands |
| 3,589,363 A | 6/1971 | Banko et al. |
| 3,693,613 A | 9/1972 | Banko et al. |
| 3,756,270 A | 9/1973 | Fonseca et al. |
| 3,818,913 A | 6/1974 | Wallach |
| 4,018,247 A | 4/1977 | Carr |
| 4,030,520 A | 6/1977 | Sands |
| 4,155,374 A | 5/1979 | Diehl |
| 4,156,187 A | 5/1979 | Murry et al. |
| 4,168,707 A | 9/1979 | Douvas et al. |
| 4,223,676 A | 9/1980 | Wuchinich et al. |
| 4,246,902 A | 1/1981 | Martinez |
| 4,274,411 A | 6/1981 | Dotson, Jr. |
| 4,380,911 A | 4/1983 | Zumbiel |
| 4,493,694 A | 1/1985 | Wuchinich |
| 4,515,583 A | 5/1985 | Sorich |
| 4,570,669 A | 2/1986 | Pauliukonis |
| 4,589,415 A | 5/1986 | Haaga |
| 4,609,368 A | 9/1986 | Dotson, Jr. |
| 4,655,247 A | 4/1987 | Westra et al. |
| 4,657,490 A | 4/1987 | Abbott |
| 4,668,231 A | 5/1987 | de Vries et al. |

(Continued)

FOREIGN PATENT DOCUMENTS

EP    1199054 A1    4/2002

(Continued)

OTHER PUBLICATIONS

John M. Bourne, Spring-Less Check Valve for a Handpiece, U.S. Appl. No. 12/237,468, Sep. 28, 2008 (18 pages).

*Primary Examiner*—Nicholas D Lucchesi
*Assistant Examiner*—Theodore J Stigell

(57) ABSTRACT

A liquefaction surgical handpiece having a check valve within the boiling chamber. Such a construction reduces upstream fluid volume. Reduction of upstream fluid volume reduces capability for compliance caused either by trapped air or absorbed gas in the liquid.

5 Claims, 2 Drawing Sheets

U.S. PATENT DOCUMENTS

| | | |
|---|---|---|
| 4,784,652 A | 11/1988 | Wikstrom |
| 4,797,098 A | 1/1989 | Kawata |
| 4,869,715 A | 9/1989 | Sherburne |
| 4,909,783 A | 3/1990 | Morrison |
| 4,921,477 A | 5/1990 | Davis |
| 4,922,902 A | 5/1990 | Wuchinich et al. |
| 4,935,005 A | 6/1990 | Haines |
| 4,989,583 A | 2/1991 | Hood |
| 5,061,241 A | 10/1991 | Stephens et al. |
| 5,154,694 A | 10/1992 | Kelman |
| 5,261,883 A | 11/1993 | Hood et al. |
| 5,322,504 A | 6/1994 | Doherty et al. |
| 5,358,150 A | 10/1994 | Scheuble et al. |
| 5,359,996 A | 11/1994 | Hood |
| 5,380,280 A | 1/1995 | Peterson |
| 5,514,088 A | 5/1996 | Zakko |
| 5,514,110 A | 5/1996 | Teh |
| 5,562,692 A | 10/1996 | Bair |
| 5,577,533 A | 11/1996 | Cook |
| 5,616,120 A | 4/1997 | Andrew et al. |
| 5,735,815 A | 4/1998 | Bair |
| 5,741,229 A | 4/1998 | Robinson et al. |
| 5,853,384 A | 12/1998 | Bair |
| 5,865,790 A | 2/1999 | Bair |
| 5,885,243 A | 3/1999 | Capetan et al. |
| 5,989,212 A * | 11/1999 | Sussman et al. .............. 604/27 |
| 5,997,499 A | 12/1999 | Sussman et al. |
| 6,004,284 A * | 12/1999 | Sussman et al. .............. 604/27 |
| 6,080,128 A | 6/2000 | Sussman et al. |
| 6,101,162 A | 8/2000 | Sussman et al. |
| 6,123,101 A | 9/2000 | Velie |
| 6,155,975 A | 12/2000 | Urich et al. |
| 6,179,805 B1 | 1/2001 | Sussman et al. |
| 6,179,808 B1 | 1/2001 | Boukhny et al. |
| 6,186,148 B1 | 2/2001 | Okada |
| 6,196,989 B1 | 3/2001 | Padget et al. |
| 6,206,848 B1 | 3/2001 | Sussman et al. |
| 6,241,700 B1 | 6/2001 | Leukanech |
| 6,258,111 B1 | 7/2001 | Ross et al. |
| 6,287,274 B1 | 9/2001 | Sussman et al. |
| 6,315,755 B1 | 11/2001 | Sussman |
| 6,331,171 B1 | 12/2001 | Cohen |
| 6,398,759 B1 | 6/2002 | Sussman et al. |
| 6,425,883 B1 | 7/2002 | Urich et al. |
| 6,440,103 B1 | 8/2002 | Hood et al. |
| 6,513,545 B2 | 2/2003 | Rhone |
| 6,575,929 B2 | 6/2003 | Sussman et al. |
| 6,575,990 B1 | 6/2003 | Wang et al. |
| 6,579,270 B2 | 6/2003 | Sussman et al. |
| 6,589,201 B1 | 7/2003 | Sussman et al. |
| 6,589,204 B1 | 7/2003 | Sussman et al. |
| 6,623,477 B1 | 9/2003 | Elbrecht et al. |
| 6,648,847 B2 | 11/2003 | Sussman et al. |
| 6,676,628 B2 | 1/2004 | Sussman et al. |
| 6,796,957 B2 | 9/2004 | Carpenter et al. |
| 6,830,064 B2 | 12/2004 | Ji |
| 6,860,868 B1 | 3/2005 | Sussman et al. |
| 6,892,756 B2 | 5/2005 | Schulze |
| 6,920,895 B2 | 7/2005 | Avis et al. |
| 6,921,385 B2 | 7/2005 | Clements et al. |
| 6,953,052 B2 | 10/2005 | Lehtonen |
| 7,160,268 B2 | 1/2007 | Darnell et al. |
| 7,509,831 B2 | 3/2009 | Khashayar |
| 7,535,815 B2 | 5/2009 | Van Den Homberg et al. |
| 2002/0013572 A1 | 1/2002 | Berlin |
| 2002/0161326 A1 | 10/2002 | Sussman et al. |
| 2002/0188261 A1 | 12/2002 | Hruska |
| 2003/0195538 A1 | 10/2003 | Wang et al. |
| 2004/0024380 A1 | 2/2004 | Darnell et al. |
| 2004/0082939 A1 | 4/2004 | Berlin |
| 2005/0228423 A1 | 10/2005 | Khashayar |
| 2005/0228424 A1 | 10/2005 | Khashayar |
| 2006/0058823 A1 | 3/2006 | Dimalanta et al. |
| 2006/0161101 A1 | 7/2006 | Dimalanta et al. |
| 2006/0173403 A1 | 8/2006 | Injer |
| 2006/0184091 A1 | 8/2006 | Dimalanta et al. |
| 2006/0212037 A1 | 9/2006 | Sussman et al. |
| 2006/0212039 A1 | 9/2006 | Sussman et al. |
| 2006/0224116 A1 | 10/2006 | Underwood et al. |
| 2008/0073906 A1 | 3/2008 | Turner |
| 2008/0077077 A1 | 3/2008 | Williams |
| 2008/0082077 A1 | 4/2008 | Williams |
| 2008/0086093 A1 | 4/2008 | Steppe et al. |
| 2008/0125697 A1 | 5/2008 | Gao |
| 2009/0032121 A1 | 2/2009 | Chon |
| 2009/0032123 A1 | 2/2009 | Bourne |
| 2009/0068870 A1 | 3/2009 | Mezhinsky |

FOREIGN PATENT DOCUMENTS

| | | |
|---|---|---|
| WO | WO 2006/101727 A1 | 9/2006 |
| WO | WO 2006/101727 A2 | 9/2006 |

* cited by examiner

PUMPING CHAMBER FOR A LIQUEFACTION HANDPIECE

BACKGROUND OF THE INVENTION

This invention relates generally to the field of ophthalmic and otic surgery and more particularly to a pumping chamber for a handpiece for ophthalmic and otic surgery.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the injection of a relatively cool solution, thereby quickly cooling and removing the heated solution. This technique is more fully described in U.S. Pat. No. 5,616,120 (Andrew, et al.), the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

One liquefaction handpiece, generally described in U.S. Pat. Nos. 5,989,212, 6,575,929 B2, and 6,676,628 B2 (all to Sussman, et al.) and commercially available as the AUQALASE® handpiece from Alcon Laboratories, Inc., Fort Worth, Tex., contains an internal boiling chamber. The pulse repetition rate of this handpiece is less than optimal because of the time required to refill the boiling chamber between pulses. The entire contents of these patents are incorporated herein by reference, specifically column 3, lines 47-67, column 4, lines 1-32 and FIGS. 7 and 8 of U.S. Pat. No. 5,989,212, column 3, lines 40-67, column 4, lines 1-32 and FIGS. 7 and 8 of U.S. Pat. No. 6,575,929 and column 3, lines 47-67, column 4, lines 1-37 and FIGS. 7 and 8 of U.S. Pat. No. 6,676,628. The handpiece disclosed in these references contains a backflow check valve upstream of the boiling chamber. Such a construction increases the time required to refill the boiling chamber once a pulse of fluid has exited the chamber.

Therefore, a need continues to exist for a control system for a surgical handpiece that can more rapid pulses of heated solution used to perform liquefaction surgical procedures.

BRIEF SUMMARY OF THE INVENTION

The present invention improves upon the prior art by providing a liquefaction surgical handpiece having a check valve within the boiling chamber. Such a construction reduces upstream fluid volume. Reduction of upstream fluid volume reduces capability for compliance caused either by trapped air or absorbed gas in the liquid.

Accordingly, one objective of the present invention is to provide a surgical handpiece having a pumping chamber with two electrodes.

Another objective of the present invention is to provide a surgical handpiece having a device for delivering the surgical fluid through the handpiece in rapid pulses.

Another objective of the present invention is to provide a liquefaction surgical handpiece having a check valve within the boiling chamber.

These and other advantages and objectives of the present invention will become apparent from the detailed description and claims that follow.

DETAILED DESCRIPTION OF THE INVENTION

Figure 1:
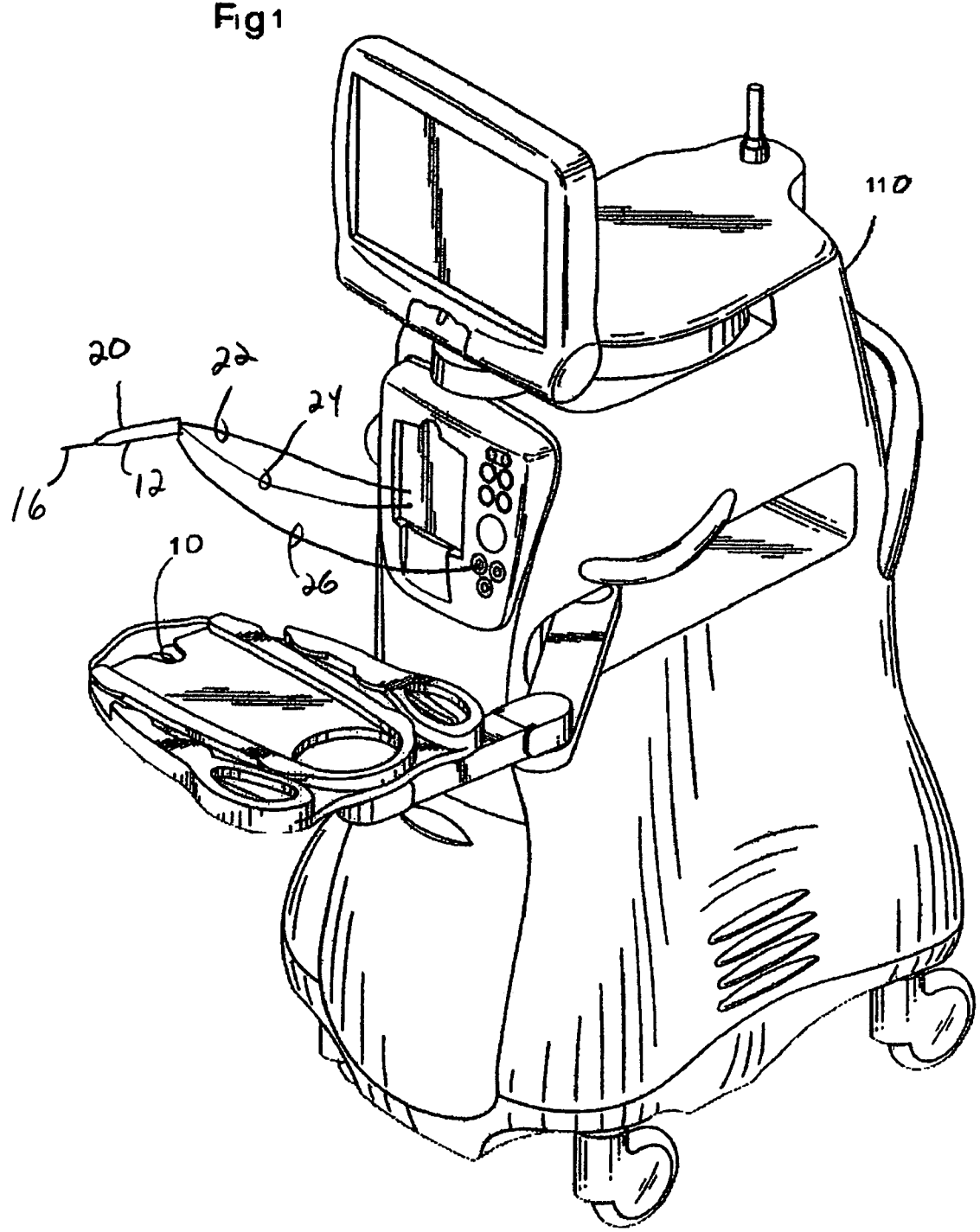
FIG. 1 is a perspective view of a surgical system that may be used with the handpiece of the present invention.

As best seen in FIG. 1, commercially available surgical systems generally include surgical console 110 having attached mayo tray 10 and handpiece 20 attached to console 110 by aspiration tubing 22, irrigation tubing 24 and power cable 26. Power to handpiece 20 as well as flows of irrigation and aspiration fluids are controlled by console 110, which contains appropriate hardware and software, such as power supplies, pumps, pressure sensors and valves, all of which are well-known in the art.

Figure 2:
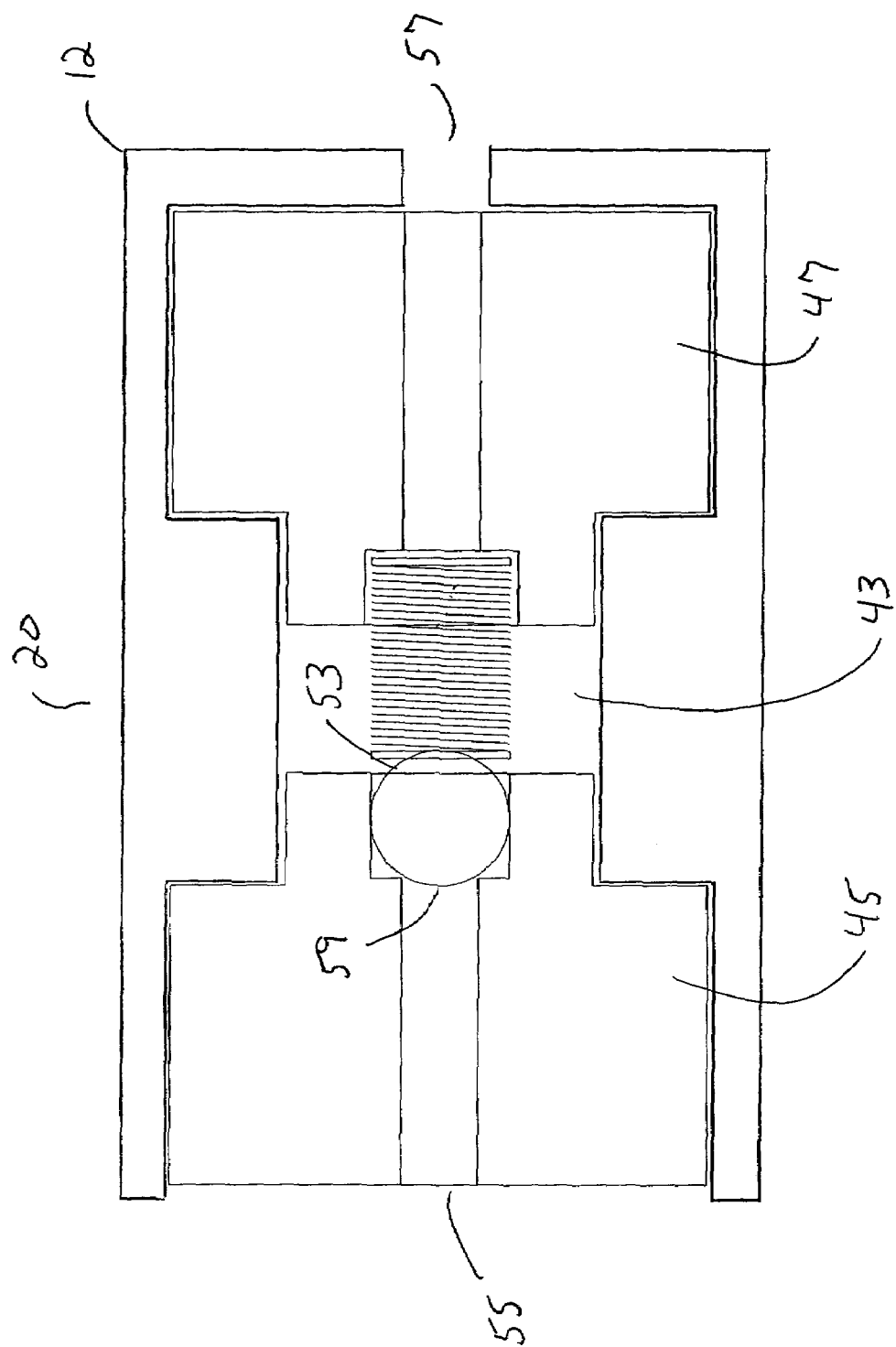
FIG. 2 is a partial cross-sectional view of the handpiece of the present invention.

Handpiece 20 of the present invention generally includes handpiece body 12 and operative tip 16. Contained within body 12, as best seen in FIG. 2, are proximal electrode 45 and distal electrode 47 which define pumping reservoir 43. Electrical power is supplied to electrodes 45 and 47 by insulated wires, not shown. In use, surgical fluid (e.g. saline irrigating solution) enters reservoir 43 through port 55, inlet 59 and check valve 53, check valves 53 being well-known in the art. Electrical current (preferably Radio Frequency Alternating Current or RFAC) is delivered to and across electrodes 45 and 47 because of the conductive nature of the surgical fluid. As the current flows through the surgical fluid, the surgical fluid boils. As the surgical fluid boils, it expands rapidly out of pumping chamber 43 through port 57 (check valve 53 prevents the fluid from expanding backwards into inlet 59. The expanding gas bubble pushes the surgical fluid in port 57 downstream of reservoir 43 forward. Subsequent pulses of electrical current form sequential gas bubbles that move surgical fluid out port 57. The size and pressure of the fluid pulse obtained out of reservoir 43 can be varied by varying the length, timing and/or power of the electrical pulse sent to electrodes 45 and 47 and by varying the dimensions of reservoir 43.

The repetition rate of the pulses generated in reservoir 43 are limited by the amount of time it take to refill reservoir 43 after a pressurized pulse has been discharge out of port 57. Many factors can affect this refill time, including resistance in irrigation tubing 24, which may be the source of fluid for reservoir 43. Placing check valve 53 within reservoir 43 reduces the length of the fluid path between check valve 53 and reservoir 43, which reduces the amount of time it takes fluid to flow from check valve 53 to reservoir 43 and reduces the upstream fluid volume which reduces the capability for compliance caused either by trapped air or absorbed gas in the liquid.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

We claim:

1. A handpiece, comprising:
   a body having an integral pumping reservoir, the pumping reservoir having an inlet and being at least partially surrounded by a pair of electrodes; and
   a check valve located at least partially within a portion of the pumping reservoir that is at least partially surrounded by the pair of electrodes;
   wherein the check valve comprises a ball and a spring and wherein the ball is at least partially supported by one electrode of the pair of electrodes and wherein the spring is at least partially supported by the other electrode of the pair of electrodes.

2. The handpiece of claim 1, wherein the ball is in contact with the one electrode of the pair of electrodes and wherein the spring is in contact with the other electrode of the pair of electrodes.

3. A handpiece, comprising:
   a first electrode;
   a second electrode;
   a pumping reservoir located between the first electrode and the second electrode, wherein the first electrode and the second electrode are configured to produce an electrical current in the pumping reservoir to boil a surgical fluid in the pumping reservoir; and
   a check valve located at least partially within the pumping reservoir;
   wherein the check valve is at least partially supported by the first electrode and the second electrode;
   wherein the check valve is in contact with the first electrode and the second electrode.

4. A handpiece, comprising:
   a first electrode;
   a second electrode;
   a pumping reservoir located between the first electrode and the second electrode, wherein the first electrode and the second electrode are configured to produce an electrical current in the pumping reservoir to boil a surgical fluid in the pumping reservoir; and
   a check valve located at least partially within the pumping reservoir;
   wherein the check valve comprises a ball and a spring and wherein the ball is at least partially supported by the first electrode and wherein the spring is at least partially supported by the second electrode.

5. The handpiece of claim 3, wherein the ball is in contact with the first electrode and wherein the spring is in contact with the second electrode.

* * * * *